US009532151B2

(12) United States Patent
Hartley et al.

(10) Patent No.: US 9,532,151 B2
(45) Date of Patent: Dec. 27, 2016

(54) BODY WORN SOUND PROCESSORS WITH DIRECTIONAL MICROPHONE APPARATUS

(75) Inventors: Lee F. Hartley, Carlsbad, CA (US); Scott A. Crawford, Castaic, CA (US)

(73) Assignee: Advanced Bionics AG, Staefa (CH)

( * ) Notice: Subject to any disclaimer, the term of this patent is extended or adjusted under 35 U.S.C. 154(b) by 134 days.

(21) Appl. No.: 14/391,825

(22) PCT Filed: Apr. 30, 2012

(86) PCT No.: PCT/US2012/035836
§ 371 (c)(1), (2), (4) Date: Nov. 21, 2014

(87) PCT Pub. No.: WO2013/165361
PCT Pub. Date: Nov. 7, 2013

(65) Prior Publication Data

US 2015/0112407 A1 Apr. 23, 2015

(51) Int. Cl.

| | |
|---|---|
| ***A61N 1/00*** | (2006.01) |
| ***H04R 25/00*** | (2006.01) |
| ***A61N 1/36*** | (2006.01) |
| *H04R 1/40* | (2006.01) |

(52) U.S. Cl.
CPC ......... *H04R 25/606* (2013.01); *A61N 1/36032* (2013.01); *H04R 25/405* (2013.01); *H04R 1/406* (2013.01); *H04R 25/402* (2013.01); *H04R 25/407* (2013.01); *H04R 2225/61* (2013.01)

(58) Field of Classification Search
CPC .......................... A61N 1/36032; A61N 1/0541
USPC ........................................................... 607/57
See application file for complete search history.

(56) References Cited

U.S. PATENT DOCUMENTS

| | | | | |
|---|---|---|---|---|
| 5,289,544 A | 2/1994 | Franklin | | |
| 7,577,266 B2 | 8/2009 | Feng et al. | | |
| 7,995,771 B1 | 8/2011 | Faltys | | |
| 2006/0015155 A1* | 1/2006 | Charvin | .............. | H04R 25/606 607/57 |
| 2007/0016267 A1* | 1/2007 | Griffin | ................ | H04R 25/505 607/57 |
| 2007/0127753 A1 | 6/2007 | Feng et al. | | |
| 2011/0096921 A1 | 4/2011 | Dyer | | |
| 2011/0116666 A1 | 5/2011 | Dittberner | | |

FOREIGN PATENT DOCUMENTS

| | | |
|---|---|---|
| DE | 19852758 A1 | 5/2000 |
| EP | 0247649 A1 | 12/1987 |
| WO | WO 2010/042326 A1 | 4/2010 |
| WO | WO 2012/010195 A1 | 1/2012 |

OTHER PUBLICATIONS

PCT International Search and Written Opinion dated Jan. 21, 2013 for PCT App. Ser. No. PCT/US2012/035836.

* cited by examiner

*Primary Examiner* — Amanda Patton
*Assistant Examiner* — Philip C Edwards
(74) *Attorney, Agent, or Firm* — Henricks, Slavin & Holmes LLP

(57) ABSTRACT

A sound processor, for use with a cochlear implant, that includes directional microphone capabilities.

18 Claims, 5 Drawing Sheets

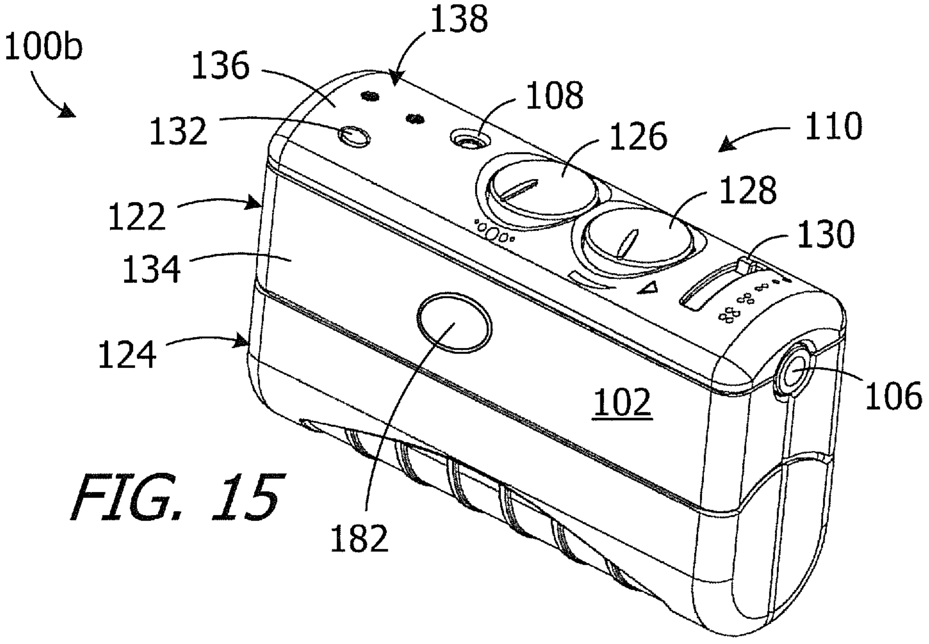
FIG. 15
FIG. 16
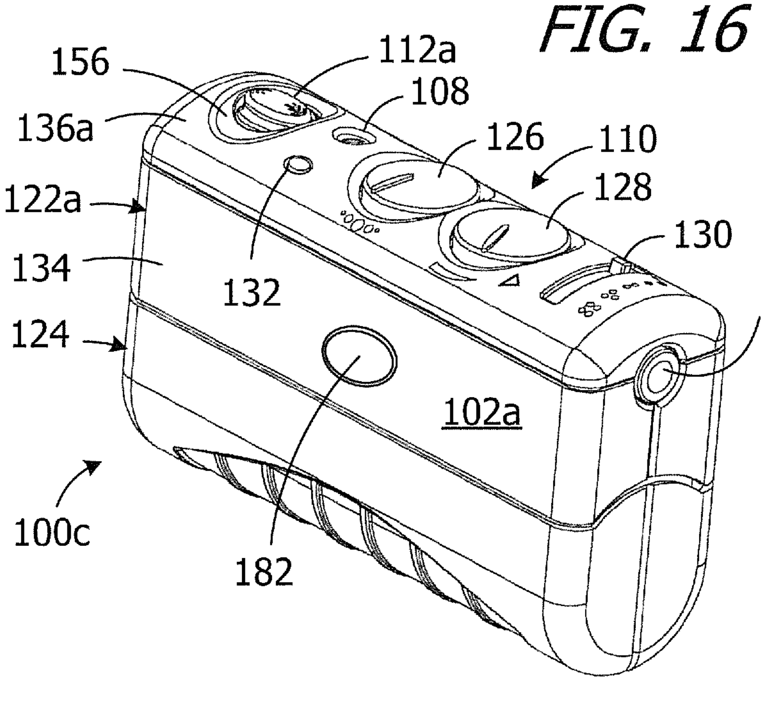

BODY WORN SOUND PROCESSORS WITH DIRECTIONAL MICROPHONE APPARATUS

CROSS-REFERENCE TO RELATED APPLICATIONS

This application is the U.S. National Stage of PCT App. Ser. No. PCT/US2012/035836, filed Apr. 30, 2012.

BACKGROUND

1. Field

The present disclosure relates generally to hearing assistance devices such as, for example, implantable cochlear stimulation ("ICS") systems.

2. Description of the Related Art

ICS systems are used to help the profoundly deaf perceive a sensation of sound by directly exciting the intact auditory nerve with controlled impulses of electrical current. Ambient sound pressure waves are picked up by an externally worn microphone and converted to electrical signals. The electrical signals, in turn, are processed by sound processor circuitry, converted to a pulse sequence having varying pulse widths and/or amplitudes, and transmitted to an implanted receiver circuit of the ICS system. The implanted receiver circuit is connected to an implantable electrode array that has been inserted into the cochlea of the inner ear, and electrical stimulation current is applied to varying electrode combinations to create a perception of sound. A representative ICS system is disclosed in U.S. Pat. No. 5,824,022, which is entitled "Cochlear Stimulation System Employing Behind-The-Ear Sound processor With Remote Control" and incorporated herein by reference in its entirety.

As alluded to above, some ICS systems include an implantable device, a sound processor, with the sound processor circuitry, and a microphone that is in communication with the sound processor circuitry. The implantable device communicates with the sound processor and, to that end, some ICS systems include a headpiece that is in communication with both the sound processor and the implantable device. The microphone may be part of the sound processor or the headpiece. In one type of ICS system, the sound processor is worn behind the ear (a "BTE sound processor"), while other types of ICS systems have a body worn sound processor unit (or "body worn sound processor"). The body worn sound processor, which is larger and heavier than a BTE sound processor, is typically worn on the user's belt or carried in the user's pocket. Body worn sound processor may also be held in a user's hand or placed on a surface such as a table at which the user is sitting. As used herein, a "body worn" sound processor is not a BTE sound processor. Examples of commercially available body worn sound processors include, but are not limited to, the Advanced Bionics Platinum Series™ body worn sound processor and the Advanced Bionics Neptune™ body worn sound processor.

One issue associated with ICS systems is ambient noise, i.e., speech or other sound from non-target sound sources ("non-target sources"), and it is desirable to suppress noise while preserving sound from the target sound source ("target source"). Beamforming is a known directional microphone technique that involves two or more microphones and can be used to preserve sound from the target source while filtering out or otherwise attenuating sound from non-target sources. BTE-based cochlear implant systems with beamforming microphone capabilities have been proposed in, for example, commonly assigned U.S. Pat. No. 7,995,771, which is incorporated herein by reference. The present inventors have determined that there are certain situations where BTE-based beamforming may be less than optimal. For example, in those instances where the user, either frequently or infrequently, turns his/her head to look at persons or objects other than the target source, a separate stationary microphone may be required. The present inventors have, therefore, determined that it would be advantageous to provide a body worn sound processor with directional microphone (e.g., beamforming) capabilities.

SUMMARY

A body worn sound processor for use with a cochlear implant in accordance with at least one of the present inventions includes a sound processor housing that is not configured to be carried on the user's ear, a microphone array, and sound processor circuitry configured to attenuate sounds received by first and second microphones that do not arrive from a direction at which the microphone array points and to generate a pulse sequence for use by the cochlear implant.

A sound processor for use with a cochlear implant in accordance with at least one of the present inventions includes a sound processor housing, a microphone array that is movable relative to the sound processor housing, and sound processor circuitry configured to attenuate sounds received by first and second microphones that do not arrive from a direction at which the microphone axis points and to generate a pulse sequence for use by the cochlear implant.

The present inventions also include cochlear stimulation systems with a cochlear implant and such sound processors.

There are a number of advantages associated with such sound processors and systems. For example, the present systems allow the user to obtain the benefits associated with directional microphone techniques by simply reorienting the sound processor or a portion thereof toward the target source. The above described and many other features of the present inventions will become apparent as the inventions become better understood by reference to the following detailed description when considered in conjunction with the accompanying drawings.

BRIEF DESCRIPTION OF THE DRAWINGS

Detailed descriptions of the exemplary embodiments will be made with reference to the accompanying drawings.

FIG. 15 is a perspective view of a body worn sound processor in accordance with one embodiment of a present invention.

FIG. 16 is a perspective view of a body worn sound processor in accordance with one embodiment of a present invention.

DETAILED DESCRIPTION OF THE EXEMPLARY EMBODIMENTS

The following is a detailed description of the best presently known modes of carrying out the inventions. This description is not to be taken in a limiting sense, but is made merely for the purpose of illustrating the general principles of the inventions.

Figure 1:
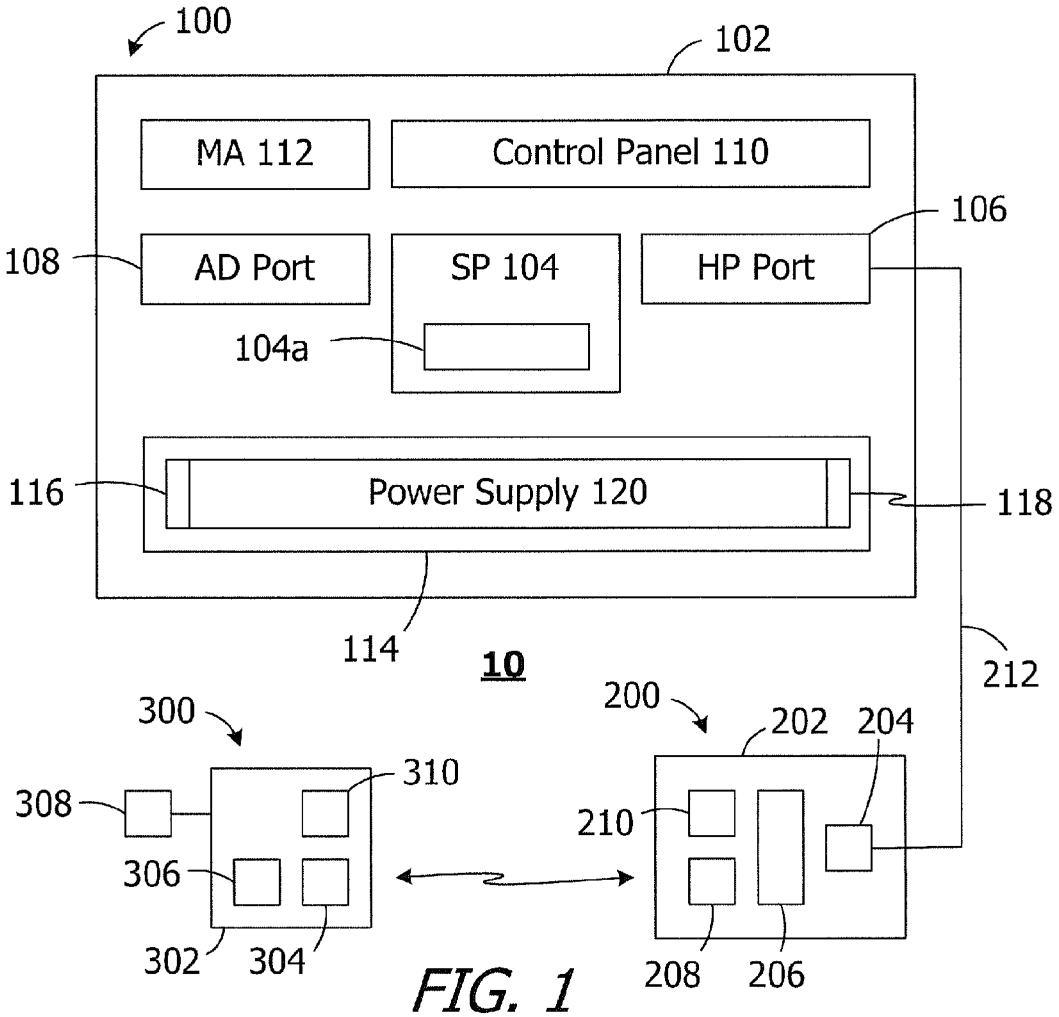
FIG. 1 is a functional block diagram of an ICS system in accordance with one embodiment of a present invention.

One example of an ICS system is the ICS system generally represented by reference numeral 10 in FIG. 1. The system 10 includes a body worn sound processor 100, a headpiece 200, and a cochlear implant 300.

The exemplary body worn sound processor 100 includes a housing 102 in which and/or on which various components are supported. Such components may include, but are not limited to, sound processor circuitry 104, a headpiece port 106, an auxiliary device port 108 for an auxiliary device such as a mobile phone or a music player, a control panel 110, a microphone array 112, and a power supply receptacle 114 with electrical contacts 116 and 118 for a removable battery or other removable power supply 120 (e.g., rechargeable and disposable batteries or other electrochemical cells). Additional details concerning the exemplary sound processor 100 are presented below in the context of FIGS. 2-5.

The exemplary headpiece 200 includes a housing 202 and various components, e.g., a RF connector 204, a microphone 206, an antenna (or other transmitter) 208 and a positioning magnet 210, that are carried by the housing. The headpiece 200 in the exemplary ICS system 10 may be connected to the sound processor headpiece port 106 by a cable 212. In at least some implementations, the cable 212 will be configured for forward telemetry and power signals at 49 MHz and back telemetry signals at 10.7 MHz. It should be noted that, in other implementations, communication between a sound processor and a headpiece and/or auxiliary device may be accomplished through wireless communication techniques. Additionally, given the presence of the microphone array 112 on the body worn sound processor 100, the microphone 206 may be also be omitted in some instances.

The exemplary cochlear implant 300 includes a housing 302, an antenna 304, an internal processor 306, a cochlear lead 308 with an electrode array, and a positioning magnet (or magnetic material) 310. The transmitter 208 and receiver 304 communicate by way of electromagnetic induction, radio frequencies, or any other wireless communication technology. The positioning magnet 210 and positioning magnet (or magnetic material) 310 maintain the position of the headpiece transmitter 208 over the cochlear implant antenna 304.

Figure 2:
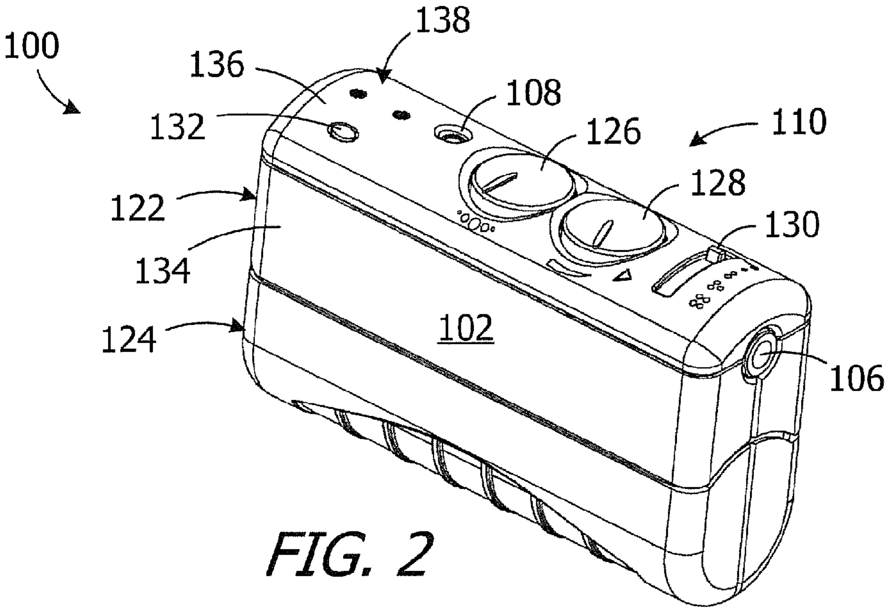
FIG. 2 is a perspective view of a body worn sound processor in accordance with one embodiment of a present invention.

Turning to FIG. 2, the exemplary sound processor housing 102 includes a main portion 122 and a power supply portion 124 that may be detachably connected to the housing main portion, as is discussed below with reference to FIG. 3. The housing main portion 122 supports and/or houses the sound processor circuitry 104, headpiece port 106, auxiliary device port 108, and the control panel 110. In the illustrated embodiment, the control panel 110 includes a sensitivity knob 126, a volume knob 128 and a program switch 130. An indicator light 132 may also be provided. The housing main portion 122 consists of a case 134 and a curved panel 136 with apertures for the auxiliary device port 108, sensitivity knob 126, volume knob 128, program switch 130, and indicator light 132. The curved panel 136 also includes two sets of microphone apertures 138 for the microphones (discussed below) in the microphone array 112. The power supply portion 124 houses the power supply receptacle 114 and power supply 120.

The sound processor housing 102 of the exemplary sound processor 100 is configured, i.e., is of suitable size, shape and weight, for body worn usage, and is not configured for BTE-type usage where the sound processor hangs on the user's ear such that the majority of the sound processor is located behind the ear. In one exemplary implementation, which is similar to the Advanced Bionics Platinum Series™ body worn sound processor in overall configuration, the housing 102 may be generally rectangular in shape and may be about 2.75 inches in length, about 0.875 inch in width, and about 1.7 inches in height, with a variation of ±30% for each dimension. In another exemplary implementation, which is similar to the Advanced Bionics Neptune™ body worn sound processor in overall configuration, the housing 102 may be generally rectangular in shape and may be about 2.3 inches in length, about 0.7 inch in width, and about 1.4 inches in height, with a variation of −10% and +30% for each dimension.

Figure 3:
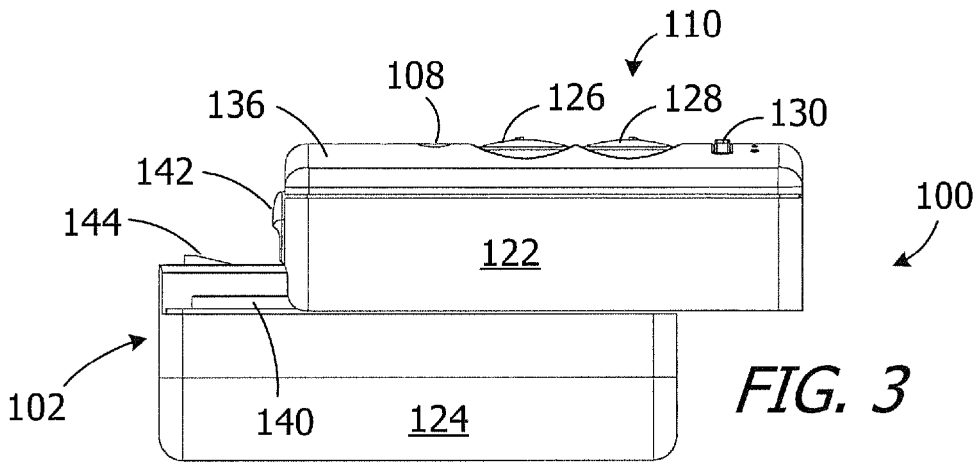
FIG. 3 is a side view of the sound processor illustrated in FIG. 2.

As illustrated in FIG. 3, the exemplary housing main portion 122 and power supply portion 124 slide in and out of engagement with one another. For example, the power supply portion 124 may be provided with projections 140 on each side that slide over and mate with corresponding projections (not shown) on the main portion 122. Electrical connectors (not shown) one the main portion 122 and power supply portion 124 will come into alignment and contact with one another when the main portion and power supply portion move from the positions illustrated in FIG. 3 to the positions illustrated in FIG. 2. The main portion 122 also includes a slidable latch 142 that engages a cam 144 on the power supply portion 124 to hold the housing portions in the positions illustrated in FIG. 2. In other implementations, the main and power supply portions may be non-separable and the battery or other power supply removed or replaced by way of a removable cover or other access device. In other implementations, the battery or other power supply may be recharged without removal from the remainder of the sound processor.

Figure 4:
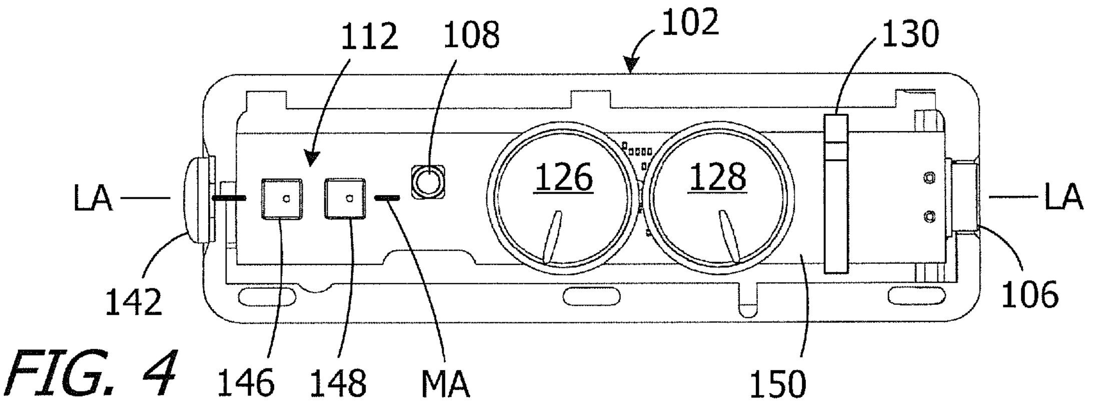
FIG. 4 is a top view of the sound processor illustrated in FIG. 2 with a portion of the housing removed.

Referring to FIG. 4, and although the present microphone arrays are not limited to a particular number of microphones, the exemplary microphone array 112 includes first and second microphones 146 and 148 that are mounted on a circuit board 150 and aligned with the microphone apertures 138. The microphones 146 and 148 are spaced along a microphone axis MA (separated by, for example, about 9.5 mm) and are fixed in place. In other words, unlike the microphone array 112*a* described below with reference to FIGS. 6-14, the microphone array 112 is not movable relative to the housing 102. The microphone axis MA is aligned with the longitudinal axis LA of the housing 102, which allows the user to aim the microphone array 112 at a target source by simply orienting the sound processor 100 such that the longitudinal axis LA is pointed at the target source.

The exemplary ICS system 10 may be operated in at least two modes, i.e., the conventional omni-directional mode where the system treats sound from all directions equally, and the directional mode where the system focuses on sound originating from a target source and attenuates sound from non-target sources. Switching between modes may be accomplished by way of a button, switch, or other user actuatable device on the sound processor (e.g., the program switch 130). In other implementations, the sound processor may be programmed to remain in the directional mode until reprogrammed. In still other implementations, the sound processor will operate in the directional mode only when a button, switch, or other user actuatable device on the sound processor is held in the actuate position (e.g., depressed in the context of a button), which allows the user to conveniently briefly switch into the directional mode as needed. One example of such sound processor is discussed below with reference to FIG. 15.

In the omni-directional mode, the microphone 206 on the headpiece 200 (or one of the microphones 146 and 148 in the microphone array 112 on the sound processor 100) picks up sound from the environment and converts it into electrical signals, and the sound processor circuitry 104 filters and manipulates the electrical signals in conventional fashion, generates a pulse sequence, and sends the pulse sequence through the cable 212 to the antenna 208. Electrical signals received from an auxiliary device are processed in essentially the same way. The receiver 304 receives pulse sequence from the antenna 208 and sends the pulse sequence to the cochlear implant internal processor 306. Corresponding current then is applied to the electrode array on the cochlear lead 308. The electrode array may be wound through the cochlea and provides direct electrical stimulation to the auditory nerves inside the cochlea. This provides the user with sensory input that is a representation of external sound waves which were sensed by the microphone 206.

Figure 5:
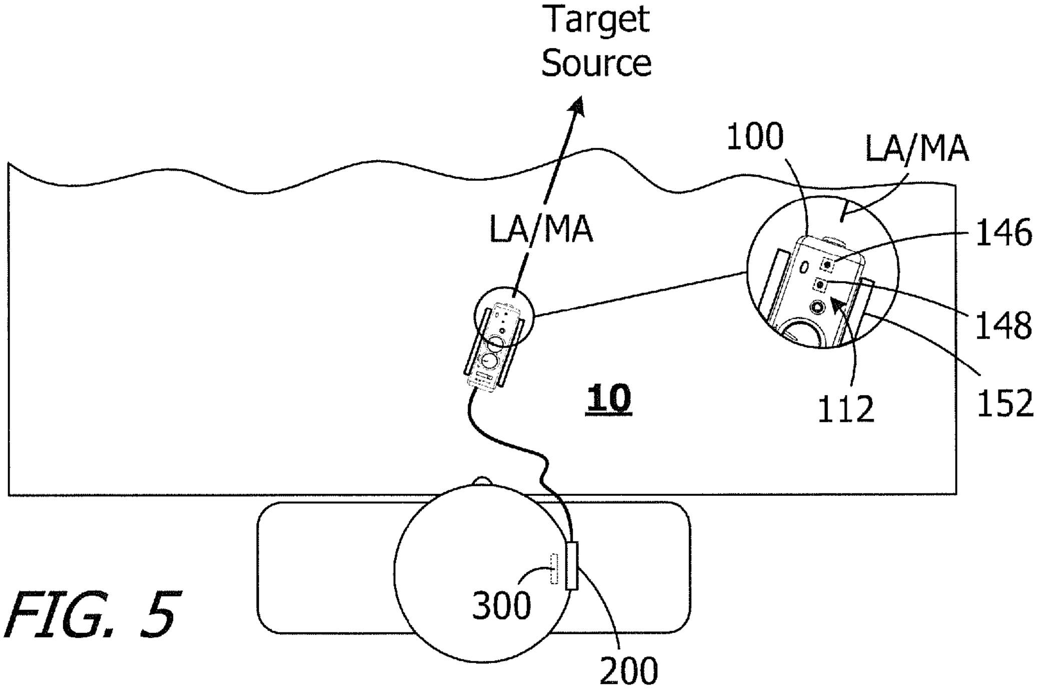
FIG. 5 is a top view of an ICS system with the sound processor positioned on a table.

Turning to FIG. 5, which shows the user of the exemplary ICS system 10 sitting at a table, the user aims the sound processor microphone array 112 at the target source when operating in the directional mode. In the illustrated embodiment, where the microphones 146 and 148 are spaced from one another along a microphone axis MA that is aligned with the longitudinal axis LA of the housing 102, the user aims microphone array 112 by orienting the sound processor 100 such that the longitudinal axis LA is pointed at the target source. The user may accomplish this by simply holding the sound processor 100 in his or her hand and pointing the longitudinal axis LA at the target source. A support device, such as the illustrated cradle 152 or a tripod, may be used to support the sound processor 100 on a table top (as shown) or other support surface. Here, the user will simply reorient the sound processor 100 relative to the target source as necessary.

With respect to sound processing in the directional mode, where the user points the microphone array 112 at the target source, the sound processor circuitry 104 includes a beamforming module 104*a* (FIG. 1) that performs the beamforming operation on the signals from the microphones 146 and 148 in, for example, the manner discussed in U.S. Pat. No. 7,995,771. Other directional sound processing examples are incorporated into the Phonak SmartLink+™ and ZoomLink+™ transmitters. Briefly, spatial processing is performed on the signals from the microphones 146 and 148, whereby signals associated with sound from the target sources at which (or near which) the microphone axis MA is pointing are enhanced and signals associated with sound from the non-target sources are attenuated. The signals are then further processed as they are in the omni-directional mode, converted to electrical impulses, and sent to the headpiece 200 and cochlear implant 300 in the manner described above in the context of the omni-directional mode.

In other implementations, a single microphone may be combined with mechanical baffling to achieve the desired directional effect. In still others, mechanical baffling and two or more microphones may be combined with the above-described beamforming techniques.

Figure 6:
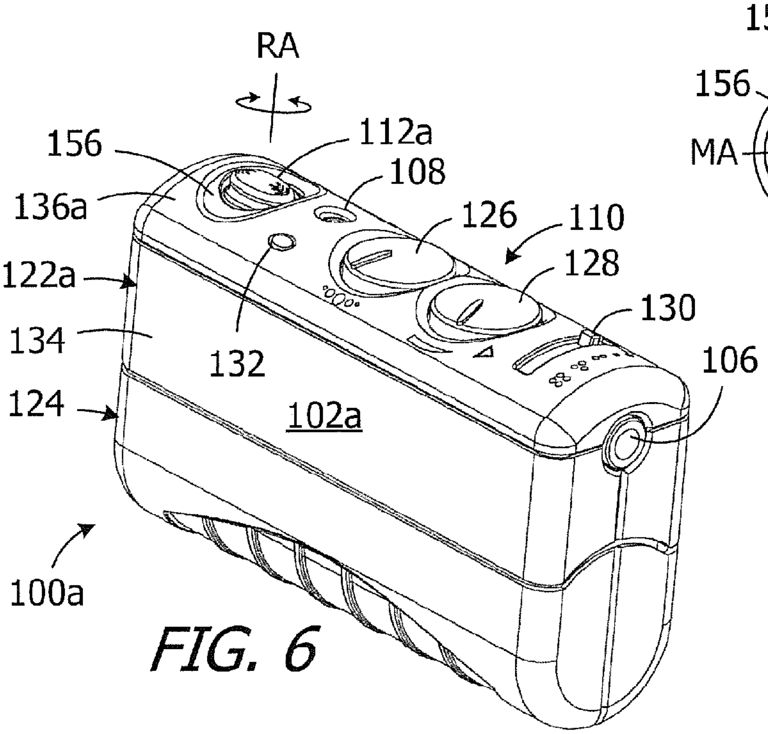
FIG. 6 is a perspective view of a body worn sound processor in accordance with one embodiment of a present invention.
Figure 7:
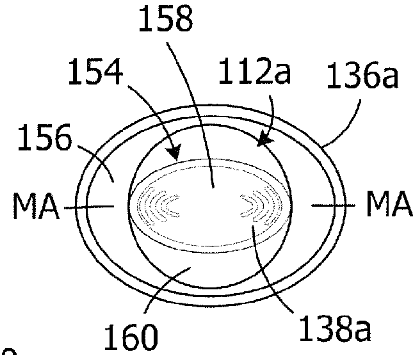
FIG. 7 is a plan view of an exemplary rotatable microphone array.
Figure 8:
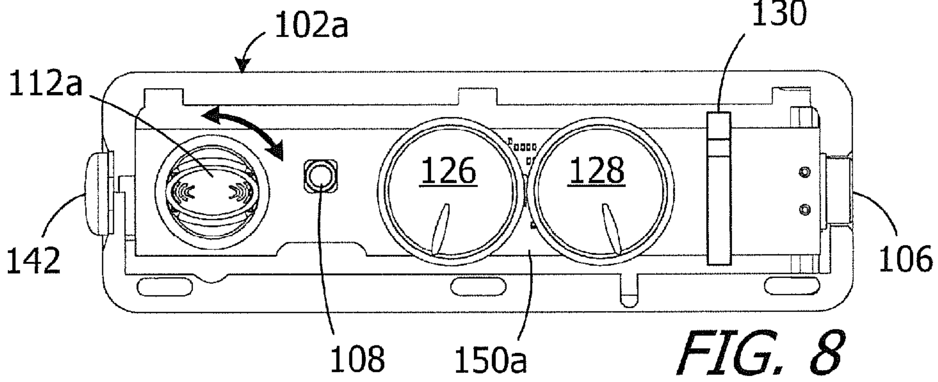
FIG. 8 is a top view of the sound processor illustrated in FIG. 6 with a portion of the housing removed.
Figure 9:
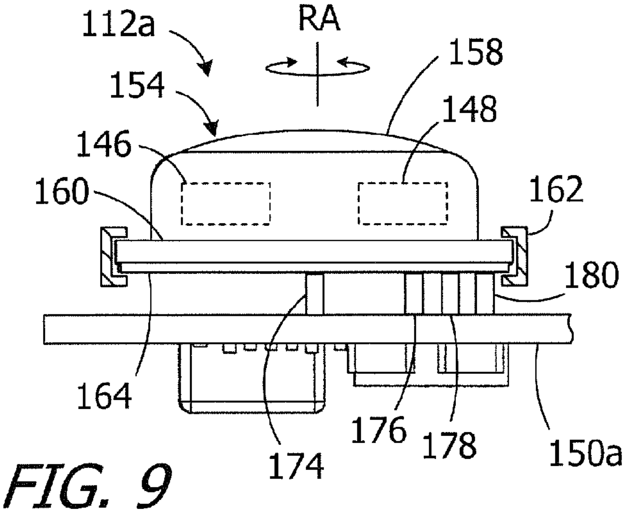
FIG. 9 is a side view of the rotatable microphone array illustrated in FIG. 7.
Figure 10:
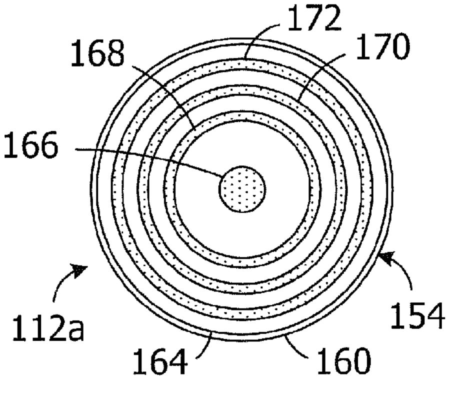
FIG. 10 is a bottom view of the exemplary rotatable microphone array illustrated in FIG. 7.

Another exemplary body worn sound processor is generally represented by reference numeral 100*a* in FIG. 6. Sound processor 100*a* is substantially similar to sound processor 100 and similar elements are represented by similar reference numerals. Here, however, the sound processor 100*a* includes a microphone array 112*a* that is movable relative to the housing 102*a*. As such, when operating in the directional mode, the user can reorient the microphone array 112*a* toward the target source without reorienting the entire sound processor. Although not limited to any particular type of movement relative to the housing, the microphone array 112*a* in the exemplary implantation illustrated in FIGS. 6-14 is rotatable relative to the sound processor housing 102*a* about a rotational axis RA. In other implementations, the microphone array may be movable in other ways. For example, the microphone array may be pivotable relative to the housing as well as rotatable to permit more accurate orientation relative to the target source.

The exemplary microphone array 112*a* includes a pair of microphones 146 and 148 that are carried within a rotatable knob 154 and define a microphone axis MA. The exemplary knob 154, which is positioned within a recess 156 in the curved panel 136*a* of the housing main portion 122*a*, has an elliptical raised portion 158 and a circular base 160. The long axis of the elliptical raised portion 158 is aligned with the microphone axis MA. Two sets of microphone apertures 138*a* are located on the top surface of the raised portion 158 in alignment with the microphones 146 and 148 and the microphone axis MA. The circular base 160 is carried within, and is rotatable relative to, a circular support 162 that is secured to the curved panel 136*a* on the housing 102*a*. In order to provide power to the microphones 146 and 148 and sound signals to the circuit board 150*a*, a circular circuit board 164 is mounted on the underside of the circular base 160 in the illustrated embodiment. The circuit board 164 includes a ground pad 166 and plurality of conductive annular pads 168-172. The ground pad 166 and conductive annular pads 168-172 are electrically connected to spring biased pins 174-180 (or other suitable connectors) on the circuit board 150*a*.

The sound processor 100*a* is also operable in the conventional omni-directional mode, and in the directional mode, as is described above with reference to sound processor 100. With respect to the orientation of the microphone array 112*a* when in the directional mode, the user has two options. The user may simply reorient the entire sound processor 100*a*, whether it is being hand held or positioned on a support surface (note FIG. 5) so that the microphone axis MA is pointed at the target source. Alternatively, the direction of the microphone array 112*a* may be adjusted by simply rotating the knob 154.

Figure 11:
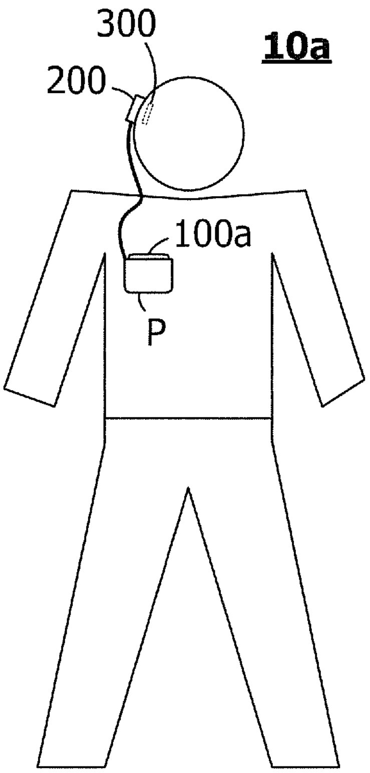
FIG. 11 is a front view of an ICS system in accordance with one embodiment of a present invention with the sound processor in the user's pocket.
Figure 12:
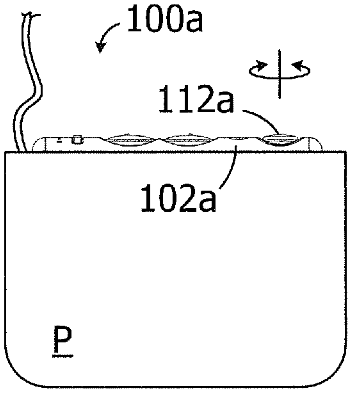
FIG. 12 is an enlarged view of a portion of FIG. 11.
Figure 13:
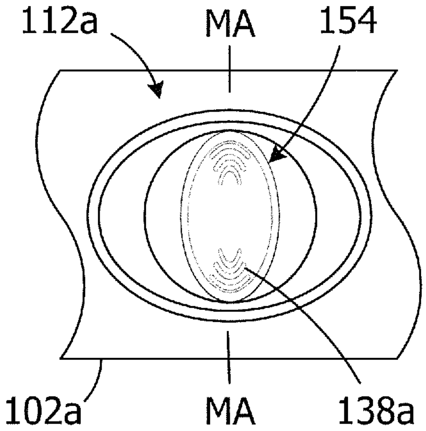
FIG. 13 is a top view of the microphone array of the sound processor illustrated in FIGS. 11 and 12.
Figure 14:
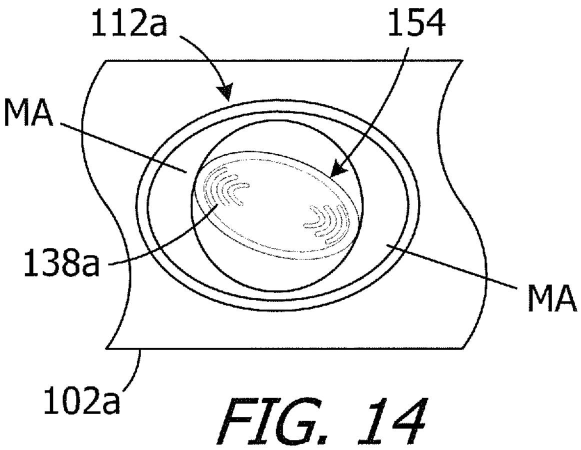
FIG. 14 is another top view of the microphone array of the sound processor illustrated in FIGS. 11 and 12.

Referring to FIGS. 11 and 12, an exemplary ICS system 10*a* includes the sound processor 100*a*, a headpiece 200 and a cochlear implant 300. The sound processor 100*a* is being worn in the user's pocket P. In those instances where the target source is located directly in front of the user (e.g., a person that is directly in front of the user), the microphone array 112*a* may be oriented in the manner illustrated in FIG. 13. Should the target source move, or should there be a new target source that is not located directly in front of the user (e.g., a different person that is not directly in front of the user), the user can redirect the microphone array 112*a* by simply rotating the knob 154 in the manner illustrated in FIG. 14 so the microphone axis MA is pointed toward the target.

Another exemplary body worn sound processor is generally represented by reference numeral 100*b* in FIG. 15. Sound processor 100*b* is substantially similar to sound processor 100 and similar elements are represented by similar reference numerals. Here, however, sound processor 100*b* includes a mode button 182 that is operably connected to the sound processor circuitry 104. The sound processor 100*b* may be configured to switch from omnidirectional mode to directional mode when the button 182 is pressed and to remain in the directional mode until the button is released. In other implementations, the sound processor will toggle from one mode to the other each time the button is pressed. The sound processor 100*a* may also be provided with a mode button. The exemplary sound processor 100*c*, which is otherwise identical to sound processor 100*a*, also include a mode button 182 that operates in the manner described here.

Although the inventions disclosed herein have been described in terms of the preferred embodiments above, numerous modifications and/or additions to the above-described preferred embodiments would be readily apparent to one skilled in the art. By way of example, but not limitation, the inventions include any combination of the elements from the various species and embodiments disclosed in the specification that are not already described. It is intended that the scope of the present inventions extend to all such modifications and/or additions and that the scope of the present inventions is limited solely by the claims set forth below.

We claim:

1. A sound processor for use with a cochlear implant, the sound processor comprising:

a sound processor housing that is not configured to be carried on the user's ear and that defines a sound processor housing longitudinal axis that extends in a direction;

a microphone array including first and second microphones carried within the sound processor housing such that the microphone array is not movable relative to the sound processor housing, and defining a microphone array axis that extends in the same direction as the sound processor housing longitudinal axis; and sound processor circuitry, operably connected to the first and second microphones and located within the sound processor housing, configured to determine whether or not sounds received by the first and second microphones arrive from a direction at which the microphone array axis points, to attenuate sounds received by the first and second microphones that do not arrive from the direction at which the microphone array axis points, and to generate a pulse sequence for use by the cochlear implant.

2. A sound processor as claimed in claim 1, wherein the housing is generally rectangular in shape and is about 2.75 inches in length, about 0.875 inch in width, and about 1.7 inches in height, with a variation of ±30% for each dimension, or the housing is generally rectangular in shape and is about 2.3 inches in length, about 0.7 inch in width, and about 1.4 inches in height, with a variation of −10% and +30% for each dimension.

3. A sound processor as claimed in claim 1, wherein the sound processor housing includes a main portion and a power supply portion that may be selectively detached from, and attached to, the main portion.

4. A sound processor as claimed in claim 1, further comprising:

a support device configured to support the sound processor housing on a support structure.

5. A sound processor as claimed in claim 1, further comprising:

means for supporting the sound processor housing on a support structure.

6. A sound processor for use with a cochlear implant, the sound processor comprising:

a sound processor housing that is not configured to be carried on the user's ear;

a rotatable knob on the sound processor housing;

a microphone array, including first and second microphones carried within the rotatable knob such that the microphone array is rotatable relative to the sound processor housing, defining a microphone array axis; and sound processor circuitry, operably connected to the first and second microphones and located within the sound processor housing, configured to attenuate sounds received by the first and second microphones that do not arrive from a direction at which the microphone array axis points and to generate a pulse sequence for use by the cochlear implant.

7. A sound processor for use with a cochlear implant, the sound processor comprising:

a sound processor housing that includes a user actuatable mode control device and is not configured to be carried on the user's ear;

a microphone array, including first and second microphones carried by the sound processor housing, defining a microphone array axis; and sound processor circuitry operably connected to the first and second microphones, operable in an omnidirectional mode and a directional mode, located within the sound processor housing, and configured to determine whether or not sounds received by the first and second microphones arrive from a direction at which the microphone array axis points, to switch from the omnidirectional mode the directional mode in response to the mode control device being actuated, to attenuate sounds received by first and second microphones that do not arrive from a direction at which the microphone array axis points only when in the directional mode, and to generate a pulse sequence for use by the cochlear implant.

8. A sound processor as claimed in claim 7, wherein the microphone array is fixedly positioned relative to the sound processor housing.

9. A sound processor as claimed in claim 8, wherein the microphone array is located within the sound processor housing.

10. A sound processor as claimed in claim 7, wherein the microphone array is movable relative to the sound processor housing.

11. A sound processor as claimed in claim 10, wherein the microphone array is rotatable relative to the sound processor housing.

12. A sound processor for use with a cochlear implant, the sound processor comprising:

a sound processor housing including a user actuatable mode control device;

a microphone array, including first and second microphones defining a microphone array axis, carried by the sound processor housing such that the microphone array is movable relative to the sound processor housing; and sound processor circuitry operably connected to the first and second microphones, operable in an omnidirectional mode and a directional mode, located within the sound processor housing, and configured to determine whether or not sounds received by the first and second microphones arrive from a direction at which the microphone array axis points, to switch from the omnidirectional mode the directional mode in response to the mode control device being actuated, to attenuate sounds received by the first and second microphones that do not arrive from the direction at which the microphone array axis points only when in the directional mode, and to generate a pulse sequence for use by the cochlear implant.

13. A sound processor as claimed in claim 12, wherein the microphone array is rotatable relative to the sound processor housing.

14. A sound processor as claimed in claim 13, wherein the microphone array is carried within a rotatable knob.

15. A sound processor as claimed in claim 14, wherein the rotatable knob defines a longitudinal axis and the microphone array axis is aligned with the longitudinal axis of the rotatable knob.

16. A sound processor as claimed in claim 12, wherein the housing is generally rectangular in shape and is about 2.75 inches in length, about 0.875 inch in width, and about 1.7 inches in height, with a variation of ±30% for each dimension, or the housing is generally rectangular in shape and is about 2.3 inches in length, about 0.7 inch in width, and about 1.4 inches in height, with a variation of −10% and +30% for each dimension.

17. A sound processor as claimed in claim 12, wherein the sound processor housing is not configured to be carried on the user's ear.

18. A sound processor as claimed in claim 12, wherein the sound processor housing includes a main portion and a power supply portion that may be selectively detached from, and attached to, the main portion.

* * * * *